United States Patent [19]

Whyman

[11] Patent Number: 4,665,222
[45] Date of Patent: May 12, 1987

[54] PRODUCTION OF ETHYLENE GLYCOL FROM SYNTHESIS GAS

[75] Inventor: Robin Whyman, Christleton, England

[73] Assignee: Imperial Chemical Industries Limited, London, England

[21] Appl. No.: 691,750

[22] Filed: Jan. 15, 1985

Related U.S. Application Data

[63] Continuation of Ser. No. 405,110, Aug. 4, 1982, abandoned, which is a continuation of Ser. No. 223,020, Jan. 6, 1981, abandoned.

[30] Foreign Application Priority Data

Jan. 31, 1980 [GB] United Kingdom ............... 8003230
Aug. 4, 1980 [GB] United Kingdom ............... 8025392

[51] Int. Cl.$^4$ ................ C07C 69/16; C07C 69/14; C07C 27/06
[52] U.S. Cl. ................ 560/263; 560/265; 518/700; 518/701
[58] Field of Search ............. 518/700, 701; 560/263, 560/265

[56] References Cited

U.S. PATENT DOCUMENTS 2,535,060 12/1950 Gresham .
2,549,470 4/1951 Howk et al. .
2,636,046 4/1953 Gresham .
3,833,634 4/1974 Pruett et al. .
3,878,290 4/1975 Walker et al. .
3,989,799 11/1976 Brown .
4,136,104 1/1979 Hwang et al. .
4,170,605 10/1979 Williamson et al. .
4,170,606 12/1979 Williamson et al. .
4,265,828 5/1981 Knifton .

FOREIGN PATENT DOCUMENTS 2024811 1/1980 United Kingdom .

OTHER PUBLICATIONS

Jenner et al, React. Kinet. Catal. Lett., vol. 15, No. 1, pp. 103–112 (1980).
Deluzarche et al, Erdol & Kohle-Erdyas, 32, 313–316 (1979).
Pruett, Annals of New York Academy of Science, 295 (1977) pp. 239–248.
Bradley, J.A.C.S., 131, 11-21-74, pp. 7419–7421.
Keim et al, J. of Catalysis, 61, 359–365 (1980).
Fonseca et al, High Pressure, Science & Technology, vol. VI, 6th Airapt Conference, Plenum Press, New York (1979) pp. 733–738.

*Primary Examiner*—Howard T. Mars
*Attorney, Agent, or Firm*—Cushman, Darby & Cushman

[57] ABSTRACT

A process for the production of ethylene glycol, methanol, ethanol and/or esters thereof from mixtures of carbon monoxide and hydrogen (synthesis gas) which comprises contacting a mixture of carbon monoxide and hydrogen with a catalyst at elevated pressure in a liquid medium, said catalyst comprising ruthenium and at least one other metal from Group VIII of the Periodic Table, and wherein the molar proportion of ruthenium is at least 50 percent relative to the other Group VIII metals. The process is particularly applicable to the selective production of ethylene glycol. The preferred catalysts, which comprise ruthenium/rhodium, may be present in elemental form, as coordination compounds or salts, e.g. carbonyls, acetyl acetonates or carboxylates. It is especially preferred to use a co-catalyst comprising a compound of one or more the metals of Groups IA, IIA or IIB or a nitrogen containing cation and/or base. Suitable liquid media include carboxylic acids (e.g. acetic acid) and ethers (e.g. tetraglyme).

13 Claims, No Drawings

PRODUCTION OF ETHYLENE GLYCOL FROM SYNTHESIS GAS

This is a continuation of application Ser. No. 405,110, filed Aug. 4, 1982 which is a continuation of Ser. No. 233,020 filed Jan. 6, 1981, both abandoned.

This invention relates to processes for the production of ethylene glycol, methanol, ethanol, and/or esters thereof, from mixtures of carbon monoxide and hydrogen, termed synthesis gas, and in particular to the selective production of ethylene glycol from synthesis gas.

Processes are known for the conversion of carbon monoxide and hydrogen at high pressure into ethylene glycol but all known processes produce a range of by-products, including particularly methanol and ethanol. It is obviously desirable to be able to produce higher yields of the main product ethylene glycol relative to the by-products and many catalysts have been developed with this aim in mind of selectivity towards the production of ethylene glycol. The majority of the known processes to which this invention relates use catalysts containing Group VIII metals, the most selective of these in the known art being rhodium. However, rhodium is an expensive metal and we have now found that a cheaper and more available metal, ruthenium may be used very effectively and rendered as selective for the production of ethylene glycol as the known processes using more expensive and less available rhodium catalysts.

The use of ruthenium catalysts in the aforesaid carbon monoxide/hydrogen processes has been described in two recently published patent specifications.

UK Patent Application No. 2,024,811A describes the preparation from synthesis gas of methyl acetate, ethyl acetate and ethylene glycol diacetate using ruthenium and/or osmium catalysts in a carboxylic acid liquid medium at a temperature of 100° C. to 350° C. and at a pressure of at least 500 psi. Preferably the reaction mixture contains a co-catalyst selected from alkali metal salts, alkaline earth metal salts, quaternary ammonium salts, iminium salts and quaternary phosphonium salts.

European Patent Application No. 013,008A gives a detailed review of the prior art and in particular describes a process for the production from synthesis gas of ethylene glycol, methanol, ethanol, or carboxylate derivatives thereof using a ruthenium carbonyl complex in a suitable solvent at a temperature of 50° C. to 400° C. and at a pressure of 500 psia to 12,500 psia. The process is preferably carried out in the presence of a promoter or co-catalyst and a wide range of "Lewis Bases" are suggested as promoters including alkali metal salts, iminium salts, pyridine and substituted pyridines and bipyridyls.

In general, however, the selectivity to ethylene glycol, and in many cases the activity, of the catalysts described in the aforesaid patent applications is low, and we have now found particular ruthenium-containing catalysts, certain of which have considerably higher selectivity to ethylene glycol and/or high activity.

According to the present invention a process for the production of ethylene glycol, methanol, ethanol, or esters thereof, which comprises contacting a mixture of carbon monoxide and hydrogen with a catalyst in a liquid medium, said catalyst comprising ruthenium and at least one other metal from Group VIII of the Periodic Table, and wherein the molar proportion of ruthenium is at least 50 percent relative to the other Group VIII metals.

The process may be carried out in either a homogeneous or a heterogeneous reaction system, the former being preferred. Accordingly, the catalyst may be present in the system as a heterogeneous phase for example as a metal or compound deposited on a solid support such as carbon, silica or alumina or may be dissolved in the liquid medium and thus form a homogeneous phase therewith.

The other Group VIII metals are preferably the metals rhodium, palladium, platinum, iridium, cobalt, and nickel; the metal especially effective in small proportions with ruthenium is rhodium. Ruthenium and the other Group VIII metals may be used in the catalyst in elemental form, as coordination compounds or as salts, preferably carbonyls, acetyl acetonates or carboxylate salts for example the acetate and benzoate salts have been found especially useful.

Preferably, the catalyst is provided with an additional component, or co-catalyst, which is a compound of one or more of the metals of Group IA, IIA or IIB of the Periodic Table or a nitrogen-containing cation and/or base. The co-catalyst is preferably a compound which is at least partially soluble in the liquid medium.

It is convenient in preparation of the catalyst when using a Group IA, IIA or IIB metal compound as co-catalyst for either the metals or oxides, hydroxides and salts thereof e.g. carbonates, bicarbonates and acetates to be dissolved in the liquid medium possibly by reaction therewith. For example, if the liquid medium were an acidic medium the compounds formed might be salts of that acid. Alternatively the compounds of the Group IA, IIA or IIB metal used in the catalyst may be prepared before use and added in that form either to the liquid medium or to the other parts of the catalyst. Suitable Group IA and IIA metal compounds for use as co-catalysts include compounds of lithium, sodium, potassium, rubidium, caesium, magnesium, calcium and barium, preferably sodium and caesium. The preferred Group IIB metal compound is a zinc compound.

Suitable nitrogen-containing cations and/or bases for use as co-catalyst include ammonium salts, e.g. ammonium salts of carboxylic acids such as ammonium acetate; quaternary ammonium salts having the general formula $(R_4N)^+X^-$, wherein R which may be the same or different, is a hydrocarbyl group, e.g. alkyl, cyclohexyl, aryl, aralkyl, alkaryl and more preferably an alkyl group containing 1 to 20 carbon atoms, e.g. methyl, ethyl, n-propyl, i-propyl, n-butyl, i-butyl and X is an anion e.g. hydroxide, nitrate, halide or carboxylate (e.g. acetate); the corresponding quaternary iminium salts having the general formula $(R_2N)^+X^-$ where R and X are as hereinbefore defined, and also including $[(R_3P)_2N]^+X^-$ e.g. bis (triphenylphosphine) iminium salts, $[(Ph_3P)_2N^-]^+X^-$; pyridine, substituted pyridines such as alkyl, alkoxy and hydroxy pyridines, e.g. 2-methyl pyridine, 2,4,6-trimethylpyridine, 2-dodecylpyridine, 2-methoxypyridine, 2,6-dimethoxypyridine, 2-hydroxypyridine, 3-hydroxypyridine, 4-methyl-2-hydroxypyridine, and 4-methyl-2,6-dihydroxypyridine; bipyridyls, e.g. 2,2'-bipyridyl, 4,4'-bipyridyl and alkyl-substituted bipyridyls; and phenanthrolines.

The liquid medium is suitably a polar solvent, for example water, ketones, alcohols, ethers (e.g. tetraglyme), carboxylic acids and anhydrides, esters including lactones (e.g. γ-butyrolactone), amides including lactones (e.g. N-methylpyrrolidone), sulphones (e.g.

sulpholane), sulphoxides (e.g. dimethylsulphoxide) and aromatic hydrocarbons and mixtures thereof. Preferred solvents include ethers, more preferably tetraglyme, and especially preferred solvents are carboxylic acids. Suitable carboxylic acids include aliphatic acids, heterocyclic acids and aromatic acids, both substituted and non-substituted. These include aliphatic monocarboxylic acids of 1–12 carbon atoms, together with aliphatic dicarboxylic acids of 2–6 carbon atoms. Substituted aliphatic monocarboxylic acids containing one or more functional substituents such as chlorine or fluorine atoms are also effective. Preferred carboxylic acids are the aliphatic acids such as formic, acetic, propionic and butyric acids and substituted aliphatic acids such as trifluoroacetic acid.

If the catalyst is a supported catalyst it should contain 0.1% to 50%, preferably 0.5% to 10% by weight of catalyst on the support. For both heterogeneous and homogeneous systems we prefer the proportion by weight of liquid medium to catalyst to be 20:1 to 1000:1. The molar ratio of ruthenium to the total of other Group VIII metals is preferably in the range from 100:1 to 2:1 especially from 20:1 to 5:1 for both supported and unsupported catalysts. The molar ratio of co-catalyst (when present) to Group VIII metals is suitably 0.05:1 to 100:1.

The process is suitably carried out at a pressure greater than 200 bars. The pressure is preferably in the range 200–3000 bars and is more preferably in the range 500–2000 bars.

The process is suitably carried out at a temperature in the range 150°–300° C. and more preferably in the range 200°–275° C. Preferably the tempreature at no time exceeds 350° C. and more preferably 320° C.

The molar ratio of carbon monoxide to hydrogen may suitably be in the range 1:5 to 5:1. The reaction may also be carried out in the presence of gaseous inert diluents, for example carbon dioxide.

The process is conveniently operated as a continuous process. In the case of a batch process the amount of carboxylic acid present in the liquid medium is suitably sufficient to provide at least one molecule per ethylene glycol residue produced in the process.

The product of the process normally includes the mono- or di- esters of the carboxylic acid and ethylene glycol and may include free ethylene glycol also. If a heterogeneous catalyst is used the components of the reaction mixture can be separated from each other and from the catalyst by conventional means for example separating the catalyst by filtration and fractionally distilling the organic components in the mixture.

When a homogeneous system is used the catalyst will remain in the residue after volatile products have been distilled out, collected and separated. The catalyst may be re-used by regeneration of suitable compounds and with fresh addition of the liquid medium.

Conveniently the catalyst may be immersed in the medium in an autoclave pressurised to the required high pressure and the mixture of reactant gases carbon monoxide and hydrogen (often referred to as synthesis gas) passed into the liquid medium. The temperature may be raised if required and maintained for the period of the reaction after which both temperature and pressure are lowered and the product mixture removed from the autoclave. The organic products may be separated by distillation and the catalyst recovered for re-use if required. Some catalyst is inevitably lost and therefore in large scale operation the initial cost of the metals used in the preparation of the catalyst is important to the economics of the process.

The desired product of the process ethylene glycol may be collected by fractional distillation from the other products methyl and ethyl alcohols. The selectivity of the process may be assessed from the ratio of the moles of ethylene glycol produced to the total moles of alcoholic products. It is observed that using the process of this invention that the ratio of moles of ethylene glycol produced to moles of methanol may be as high as 1.84 and that this figure compares favourably with the best results reported from the use of the more expensive metal rhodium as the major Group VIII metal in prior art processes.

The hydroxyl-containing products of the process glycols and alcohols are often produced at least in part as the esters of any acidic compounds present in the system, for example the acid present in the liquid medium. Therefore the separation of the products may involve the separation of the esters and then the hydrolysis of the ester to produce the glycol (or the alcohol) separately.

The process of the invention may be operated so that the esterification of the glycol product is optimised at the mono ester stage and this may be converted readily into either ethylene oxide and/or vinyl acetate; or ethylene glycol. Thus there is some versatility possible in the nature of the product obtained.

The invention is illustrated by the following Examples.

EXAMPLES 1–17; COMPARATIVE EXAMPLE C1

A typical experiment was conducted as follows. Triruthenium dodecacarbonyl (0.52 g, 2.44 mmoles), tetrarhodium dodecacarbonyl (0.04 g, 0.21 mmoles), sodium acetate trihydrate (1.0 g, 7.35 mmoles) and glacial acetic acid (52.5 g, 50 ml) were charged into a 100 ml capacity glass liner fitted with a flip-flop glass stirrer. This assembly was transferred into a Hastelloy C lined stainless steel autoclave of 200 ml capacity. The autoclave was sealed and after being purged four times with a $CO/H_2$ mixture was pressurised to 470–490 bars with synthesis gas in a 1:1 ratio of $CO:H_2$. The autoclave was surrounded by a furnace which had been preheated to 260° C. and the system allowed to stabilise for 1 hour at 235°–240° C. during which the pressure steadied at 650 bars. The pressure was then increased to 1550 bars and maintained at 1450–1550 bars by topping up with fresh gas over a 5 hour period. During this time a total pressure drop of 770 bars was recorded. After cooling overnight the excess pressure was slowly vented and the reaction product carefully discharged. The weight of reaction product (61.5 g) corresponded to a weight increase of ca 7.5 g over the 5 hour period. Analysis of the products by gas chromatography using temperature programmed 5% Reoplex on Chromosorb G column showed ethylene glycol diacetate (71.9 mmoles), ethylene glycol monoacetate (39.0 mmoles) methyl acetate (99.4 mmoles) and ethyl acetate (28.9 mmoles) to be the major products.

The figures in parenthesis refer to the experimental conditions for Example 9 only shown in Table 1.

Other catalyst materials and different proportions were examined using the same procedure as described and the results obtained are summarised in other lines of Table 1.

As an alternative procedure the metals ruthenium and rhodium were introduced in the form of carboxylate salts especially the acetate salts for example μ-oxotri ruthenium acetate [Ru₃O(OCOCH₃)₆(H₂O)₃][OCOCH₃] (sample analysis: Ru=37.3% and Na=1.6%) and di rhodium tetraacetate (Rh=41.0%, Na=0.40%). The experimental procedure and conditions used were essentially the same as for the carbonyl compounds and the results are summarised in Table 1 in Examples 1-8, 10-16 and in Comparative Example C1 (in which the catalyst was ruthenium only).

The results shown in Table 1 (Examples 1-16) illustrate the increased selectivity to ethylene glycol and the higher activity when using catalysts comprising ruthenium/rhodium and co-catalysts.

A comparison of Example 17 and the Comparative Example C1 shows that in the presence of rhodium increased yields of methyl acetate can be obtained whilst maintaining a constant yield of ethylene glycol. In order to obtain high selectivities to ethylene glycol however, the presence of a co-catalyst is advantageous.

flip-flop glass stirrer. This assembly was transferred into a Hastelloy C lined stainless steel autoclave of 200 ml capacity. The autoclave was sealed and after being purged four times with a CO/H₂ mixture was pressurised to 470–490 bars with synthesis gas in a 1:1 ratio of CO:H₂. The autoclave was surrounded by a furnace which had been preheated to 260° C. and the system allowed to stabilise for 1 hour at 235°–240° C. during which the pressure steadied at 650 bars. The pressure was then increased to 1550 bars and maintained at 1450–1550 bars by topping up with fresh gas over a 2½ hour period.

During this time a total pressure drop of 470 bars was recorded. After cooling overnight the excess pressure was slowly vented and the reaction product carefully discharged. The weight of reaction product (57.0 g) corresponded to a weight increase of ca 3.5 g over the 2½ hour period. Analysis of the products by gas chromatography using a temperature programmed 5% Reoplex on Chromosorb G column showed ethylene glycol

TABLE 1

| | Catalyst Components (mmoles) | | | | | Product Analysis (mmoles) | | | | | |
|---|---|---|---|---|---|---|---|---|---|---|---|
| Ex No | Ru | Rh | Gp I/II Metal Salt Added | Total Gp I/II metal present | Pressure Drop Bars | MeOAc | EtOAc | EG Diacetate | EG Monoacetate | Σ CH₂OH \| CH₂OH | Ratio EG/MeOH |
| 1 | 2.0 | 0 | — | 3.6 | 600 | 109.1 | 12.2 | 51.2 | 21.3 | 72.5 | 0.66 |
| 2 | 4.0 | 0 | — | 7.2 | 960 | 160.9 | 11.3 | 51.4 | 33.5 | 84.9 | 0.53 |
| 3 | 2.0 | 0 | 10.0 NaOAc.3H₂O | 10.4 | 310 | 75.9 | 16.1 | 27.7 | 13.2 | 40.9 | 0.54 |
| 4 | 2.0 | 0.1 | 10.0 NaOAc.3H₂O | 10.4 | 370 | 71.6 | 32.4 | 46.0 | 19.2 | 65.2 | 0.91 |
| 5 | 2.0 | 0.2 | 10.0 NaOAc.3H₂O | 10.4 | 790 | 76.9 | 41.1 | 73.5 | 39.0 | 112.5 | 1.46 |
| 6 | 2.0 | 0.4 | 10.0 NaOAc.3H₂O | 10.4 | 725 | 92.2 | 40.9 | 65.3 | 35.8 | 101.1 | 1.10 |
| 7 | 2.43 | 0.24 | — | 2.1 | 730 | 148.8 | 22.6 | 56.5 | 30.7 | 87.2 | 0.59 |
| 8 | 2.43 | 0.24 | 7.4 NaOAc.3H₂O | 9.5 | 670 | 81.6 | 31.3 | 75.5 | 37.7 | 113.2 | 1.39 |
| 9 | 2.44 | 0.21 | 7.4 NaOAc.3H₂O | 7.4 | 770 | 99.4 | 28.9 | 71.9 | 39.0 | 110.9 | 1.12 |
| 10 | 4.57 | 0.23 | — | 4.1 | 1270 | 252.8 | 18.9 | 85.4 | 78.7 | 164.1 | 0.65 |
| 11 | 1.21 | 0.12 | 18.4 NaOAc.3H₂O | 19.5 | 605 | 61.9 | 42.4 | 56.9 | 24.5 | 81.4 | 1.32 |
| 12 | 2.0 | 0.2 | 10.0 NaOAc.3H₂O | 10.4 | 530 | 77.8 | 33.5 | 48.2 | 18.7 | 66.9 | 0.86 |
| 13 | 2.0 | 0.2 | 10.0 NaOCOPh | 10.4 | 460 | 74.1 | 36.3 | 65.5 | 24.4 | 89.9 | 1.21 |
| 14 | 2.0 | 0.2 | 5.0 Cs₂(CO₃).2H₂O | 10.4 | 1055 | 121.9 | 57.0 | 97.7 | 46.3 | 144.0 | 1.18 |
| 15 | 2.0 | 0.2 | 10.0 Cs OCOPh | 10.4 | 840 | 121.2 | 51.3 | 89.5 | 39.4 | 128.9 | 1.06 |
| 16 | 2.0 | 0.2 | 10.0 Mg(OAc)₂.4H₂O | 10.4 | 595 | 150.3 | 15.2 | 76.3 | 21.3 | 97.6 | 0.65 |
| 17 | 2.0 | 0.2 | — | 0 | 175 | 123.4 | 3.9 | 10.0 | 0.8 | 10.8 | 0.09 |
| C1 | 2.0 | 0 | — | 0 | 90 | 108.1 | 3.7 | 10.2 | 1.1 | 11.3 | 0.10 |

Notes on Table 1
1. Reaction conditions were 1500 bars pressure at CO/H₂ (1:1) at 235-240° C. for 5 hours, except Example 12 in which the pressure was maintained at 1300 bars throughout.
2. Ru and Rh added as [Ru₃O(OCOCH₃)₆(H₂O)₃][OCOCH₃] and [Rh₂(OCOCH₃)₄.2MeOH] respectively except in Examples 9 and 17 where Ru₃(CO)₁₂ and Rh₄(CO)₁₂ were used and Example C1 where Ru₃(CO)₁₂ was used.
3. The figures in the columns entitled Group I/II metal salt and total Group I/II metal do not in general agree. This is because additional sodium is present in ruthenium acetate used as starting material for the catalyst.
4. Other products such as methyl formate and n-propyl acetate are also formed but are present in minor amounts, typically less than 2 mmole.

EXAMPLES 18-24; COMPARATIVE EXAMPLE C2

These examples illustrate the use of ruthenium/rhodium catalysts in combination with co-catalysts comprising nitrogen-containing cations and/or bases. A typical experiment was conducted as follows. Trisacetyl acetonatoruthenium (0.8 g 2.0 mmoles), tetraacetatodirhodium (0.05 g 0.2 mmoles), pyridine (0.16 g 2.0 mmoles) and glacial acetic acid (52.5 g, 50 ml) were charged into a 100 ml capacity glass liner fitted with a diacetate (46.6 mmoles), ethylene glycol monoacetate (26.8 mmoles), methyl acetate (52.2 mmoles and ethyl acetate (10.2 mmoles to be the major products. The figures in parenthesis refer to the experimental conditions for Example 22 only shown in Table 2.

Other catalyst materials and different proportions were examined using the same procedure as described and the results obtained are summarised in Table 2, along with result of Comparative Example C2 which illustrates the low selectivity to ethylene glycol and the low activity when using [Ph₄As]OAc as co-catalyst.

TABLE 2

| | Catalyst components mmoles | | | Pressure Drop Bars | Product Analysis (mmoles) | | | | | |
|---|---|---|---|---|---|---|---|---|---|---|
| Ex No | Ru | Rh | Additive | | MeOAc | EtOAc | EG Diacetate | EG Monoacetate | Σ CH₂OH \| CH₂OH | EG/MeOH |
| 18 | 2.0 | 0.2 | 2.0 [(Ph₃P)₂N]OAc | 485 | 97.2 | 0 | 60.0 | 27.6 | 87.6 | 0.90 |
| 19 | 2.0 | 0.2 | 2.0 [n-Bu₄N]OAc | 560 | 84.4 | 0 | 56.5 | 31.8 | 88.3 | 1.05 |
| 20 | 2.0 | 0.2 | 2.0 [NH₄]OAc | 550 | 52.2 | 13.9 | 62.9 | 33.2 | 96.1 | 1.84 |
| 21 | 1.0 | 0.1 | 1.0 [NH₄]OAc | 210 | 32.2 | 0.7 | 13.7 | 6.8 | 20.5 | 0.64 |
| 22 | 2.0 | 0.2 | 2.0 pyridine | 470 | 52.2 | 10.2 | 46.6 | 26.8 | 73.4 | 1.41 |

TABLE 2-continued

| Ex No | Catalyst components mmoles | | | Pressure Drop Bars | Product Analysis (mmoles) | | | | | |
|---|---|---|---|---|---|---|---|---|---|---|
| | Ru | Rh | Additive | | MeOAc | EtOAc | EG Diacetate | EG Monoacetate | $\Sigma \begin{array}{c} CH_2OH \\ | \\ CH_2OH \end{array}$ | EG/ MeOH |
| 23 | 2.0 | 0.2 | 2.0 2-hydroxypyridine | 640 | 105.6 | 23.7 | 64.2 | 24.4 | 88.6 | 0.84 |
| 24 | 2.0 | 0.2 | 2.0 3-hydroxypyridine | 425 | 115.9 | 0 | 46.5 | 6.0 | 52.5 | 0.45 |
| C2 | 2.0 | 0.2 | 2.0 [Ph$_4$As]OAc | 180 | 67.2 | 22.8 | 3.3 | 2.1 | 5.4 | 0.08 |

Notes on Table 2
1. Reaction conditions were 1500 ± 50 bars pressure of CO/H$_2$ (1:1) at 235-240° C. for 2½ hours
2. Ruthenium and rhodium were added as ruthenium tris-acetylacetonate [Ru(acac)$_3$] and rhodium acetate [Rh$_2$(OAc)$_4$.2MeOH] respectively
3. Other products such as methyl formate and n-propyl acetate are also formed but are present in minor amounts, typically less than 2 mmole.

EXAMPLES 25–33

These examples further illustrate the use of ruthenium/rhodium catalysts in combination with Groups IA, IIA and IIB metal compound co-catalysts. The results are summarised in Table 3.

A typical experiment was conducted as follows. Trisacetylacetonato-ruthenium (0.80 g, 2.0 mmoles), tetraacetatodirhodium (0.05 g, 0.2 mmoles), zinc acetate dihydrate (0.44 g, 2.0 mmoles) and glacial acetic acid (52.5 g, 50 ml) were charged into a 100 ml capacity glass liner fitted with a flip-flop glass stirrer. This assembly was transferred into a Hastelloy C lined stainless steel autoclave of 200 ml capacity. The autoclave was sealed and after being purged four times with a CO/H$_2$ mixture was pressurised to 470–490 bars with synthesis gas in a 1:1 ratio of CO:H$_2$. The autoclave was surrounded by a furnace which had been preheated to 260° C. and the system allowed to stabilise for 1 hour at 235°–240° C. during which the pressure steadied at 650 bars. The pressure was then increased to 1550 bars and maintained at 1450–1550 bars by topping up with fresh gas over a 2½ hour period. During this time a total pressure drop of 670 bars was recorded. After cooling overnight the excess pressure was slowly vented and the reaction product carefully discharged. The weight of reaction product (60.0 g) corresponded to a weight increase of ca. 6.2 g over the 2½ hour period. Analysis of the products by gas chromatography using a temperature programmed 5% Reoplex on Chromosorb G column showed ethylene glycol diacetate (65.5 mmoles), ethylene glycol monoacetate (23.7 mmoles), methyl acetate (59.7 mmoles) and ethyl acetate (13.0 mmoles) to be the major products.

The figures in parenthesis refer to the experimental conditions for Example 32 only (as shown in Table 3).

EXAMPLES 34–39; COMPARATIVE EXAMPLES C3 AND C4

These examples further illustrate the use of ruthenium/rhodium catalysts in combination with 2,2'-bipyridyl as co-catalyst. The results are shown in Table 4.

A typical experiment (Example 34) was conducted as follows. Tris-acetyl acetonato-ruthenium (0.8 g, 2.0 mmoles), tetracetatodirhodium (0.05 g, 0.2 mmoles), 2,2'-bipyridyl (0.31 g, 2.0 mmoles) and glacial acetic acid (52.5 g, 50 ml) were charged into a 100 ml capacity glass liner fitted with a flip-flop glass stirrer. This assembly was transferred into a Hastelloy C lined stainless steel autoclave of 200 ml capacity. The autoclave was sealed and after being purged four times with a CO/H$_2$ mixture was pressurised to 470–490 bars with synthesis gas in a 1:1 ratio of CO:H$_2$. The autoclave was surrounded by a furnace which had been preheated to 260° C. and the system allowed to stabilise for 1 hour at 235°–240° C. during which the pressure steadied at 650 bars. The pressure was then increased to 1550 bars and maintained at 1450–1550 bars by topping up with fresh gas over a 2½ hour period.

During this time a total pressure drop of 510 bars was recorded. After cooling overnight the excess pressure was slowly vented and the reaction product carefully discharged. The weight of reaction product (59.5 g) corresponded to a weight increase of ca. 5.8 g over the 2½ hour period. Analysis of the products by gas chromatography using a temperature programmed 5% Reoplex on Chromosorb G column showed ethylene glycol diacetate (76.6 mmoles) ethylene glycol monoacetate (35.2 mmoles), methyl acetate (91.6 mmoles) and ethyl acetate (22.6 mmoles) to be the major products.

Referring to Table 4, Examples 36–39 illustrate that decreasing the concentration of ruthenium in the Ru/Rh/2,2'-bipyridyl catalysts decreases both their activity and selectivity to ethylene glycol.

TABLE 3

| Ex No | Catalyst components mmoles | | | Pressure Drop Bars | Product Analysis (mmoles) | | | | | |
|---|---|---|---|---|---|---|---|---|---|---|
| | Ru | Rh | Additive | | MeOAc | EtOAc | EG Diacetate | EG Monoacetate | $\Sigma \begin{array}{c} CH_2OH \\ | \\ CH_2OH \end{array}$ | EG/ MeOH |
| 25 | 2.0 | 0.2 | 2.0 LiOAc.2H$_2$O | 320 | 75.0 | 0 | 34.5 | 12.2 | 46.7 | 0.62 |
| 26 | 2.0 | 0.2 | 2.0 RbOAc | 465 | 96.9 | 11.7 | 63.4 | 13.9 | 77.3 | 0.80 |
| 27 | 2.0 | 0.2 | 1.0 Cs$_2$CO$_3$.2H$_2$O | 465 | 62.2 | 20.0 | 86.8 | 17.6 | 104.3 | 1.68 |
| 28 | 2.0 | 0.2 | 1.0 Cs$_2$CO$_3$.2H$_2$O | 450 | 60.0 | 12.2 | 71.1 | 20.8 | 91.9 | 1.53 |
| 29 | 2.0 | 0.2 | 2.0 Mg(OAc)$_2$4H$_2$O | 425 | 130.0 | 0 | 20.5 | 3.7 | 24.2 | 0.19 |
| 30 | 2.0 | 0.2 | 2.0 Ba(OAc)$_2$ | 350 | 70.9 | 8.3 | 51.1 | 22.1 | 73.2 | 1.03 |
| 31 | 2.0 | 0.2 | 1.0 Zn(OAc)$_2$.2H$_2$O | 540 | 157.2 | 2.0 | 33.4 | 7.7 | 41.1 | 0.26 |
| 32 | 2.0 | 0.2 | 2.0 Zn(OAc)$_2$.2H$_2$O | 670 | 59.7 | 13.0 | 65.5 | 23.7 | 89.2 | 1.49 |
| 33 | 2.0 | 0.2 | 10.0 Zn(OAc)$_2$.2H$_2$O | 470 | 64.1 | 14.4 | 46.1 | 16.6 | 62.7 | 0.98 |

Notes on Table 3
1. Reaction conditions were 1500 ± 50 bars pressure of CO/H$_2$ (1:1) at 235-240° C. for 2½ hours.
2. Ruthenium and rhodium were added as ruthenium tris-acetylacetonate [Ru(acac)$_3$] and rhodium acetate [Rh$_2$(OAc)$_4$.2MeOH] respectively.
3. Other products such as methyl formate and n-propyl acetate are also formed but are present in minor amounts, typically less than 2 mole.

A comparison of Examples 36, C3 and C4 illustrates the high activity and selectivity to ethylene glycol using a Ru/Rh/2,2'-bipyridyl catalyst (Example 36) whereas the Ru/2,2'-bipyridyl catalyst (C3) shows a substantial reduction in activity and a very large reduction in selectivity to ethylene glycol, and the Rh/2,2'-bipyridyl catalyst (C4) shows a very large reduction in activity together with a reduction in selectivity.

EXAMPLES 44–48

These examples illustrate the use of catalysts containing platinum group metals other than rhodium in combination with ruthenium.

The results shown in Table 6 illustrate that catalysts containing ruthenium in combination with platinum group metals other than rhodium are also effective for the formation of oxygenated products.

TABLE 4

| Ex No | Catalyst components mmoles Ru | Rh | Additive | Pressure Drop Bars | MeOAc | EtOAc | EG Diacetate | EG Monoacetate | $\Sigma \begin{array}{c} CH_2OH \\ \| \\ CH_2OH \end{array}$ | EG/ MeOH |
|---|---|---|---|---|---|---|---|---|---|---|
| 34 | 2.0 | 0.2 | 2.0 2,2'-bipyridyl | 510 | 91.6 | 22.6 | 76.6 | 35.2 | 111.8 | 1.22 |
| 35 | 2.0 | 0.2 | 0.5 2,2'-bipyridyl | 475 | 71.3 | 12.8 | 50.0 | 18.4 | 68.4 | 0.96 |
| 36 | 2.0 | 0.2 | 1.0 2,2'-bipyridyl | 525 | 93.7 | 20.7 | 81.8 | 52.4 | 134.2 | 1.43 |
| 37 | 1.0 | 0.2 | 1.0 2,2'-bipyridyl | 330 | 46.9 | 12.4 | 38.2 | 21.5 | 59.7 | 1.27 |
| 38 | 0.5 | 0.2 | 1.0 2,2'-bipyridyl | 140 | 32.2 | 12.4 | 43.2 | 0 | 43.2 | 1.34 |
| 39 | 0.2 | 0.2 | 1.0 2,2'-bipyridyl | 270 | 33.1 | 9.3 | 29.8 | 6.3 | 36.1 | 1.09 |
| C3 | 2.0 | 0 | 1.0 2,2'-bipyridyl | 140 | 61.6 | 10.4 | 11.3 | 2.3 | 13.6 | 0.22 |
| C4 | 0 | 0.2 | 1.0 2,2'-bipyridyl | 90 | 18.8 | 5.4 | 14.7 | 1.6 | 16.3 | 0.87 |

Notes on Table 4
1. Reaction conditions were 1500 ± 50 bars pressure of CO/H$_2$ (1:1) at 235–240° C. for 2½ hours.
2. Ruthenium and rhodium were added as ruthenium tris-acetylacetonate [Ru(acac)$_3$] and rhodium acetate [Rh$_2$(OAc)$_4$.2MeOH] respectively.
3. Other products such as methyl formate and n-propyl acetate were also formed but are present in minor amounts, typically less than 2 mmole.

TABLE 6

| Ex No | Catalyst components mmoles Ru | Pt Group Metal | Additive | Pressure Drop Bars | MeOAc | EtOAc | EG Diacetate | EG Monoacetate | $\Sigma \begin{array}{c} CH_2OH \\ \| \\ CH_2OH \end{array}$ | EG/ MeOH |
|---|---|---|---|---|---|---|---|---|---|---|
| 44 | 2.0 | 0.2 Pd | 2.0 Cs | 525 | 75.6 | 11.5 | 34.2 | 15.7 | 49.9 | 0.66 |
| 45 | 2.0 | 1.0 Pd | 2.0 Cs | 345 | 68.8 | 11.1 | 33.4 | 12.3 | 45.7 | 0.66 |
| 46 | 2.0 | 0.2 Pt | 2.0 Cs | 195 | 57.2 | 0.7 | 5.7 | 0 | 5.7 | 0.10 |
| 47 | 2.0 | 1.0 Pt | 2.0 Cs | 430 | 35.9 | 5.7 | 7.3 | 0 | 7.3 | 0.20 |
| 48 | 2.0 | 0.2 Ir | 2.0 Cs | 220 | 50.9 | 6.3 | 6.8 | 0 | 6.8 | 0.13 |

Notes on Table 6
1. Reaction conditions were 1500 ± 50 bars pressure of CO/H$_2$ (1:1) at 235–240° C. for 2½ hours.
2. Caesium added as Cs$_2$CO$_3$2H$_2$O Ruthenium added as ruthenium tris-acetylacetonate [Ru(acac)$_3$] Palladium added as palladium acetate [Pd(OAc)$_2$] Platinum added as platinum bis-acetylacetonate [Pt(acac)$_2$] Iridium added as tetrairidium dodecarbonyl [Ir$_4$(CO)$_{12}$]

EXAMPLES 40–43

These examples illustrate the beneficial effect of increasing pressure on both the activity and selectivity to ethylene glycol when using ruthenium/rhodium catalysts in combination with 2,2'-bipyridyl as co-catalyst. The results are summarised in Table 5.

An increase in total working pressure from 750 bars to 1500 bars (Examples 43 to 40) results in the Ru/Rh/2,2'-bipyridyl catalysts having higher activity and selectivity to ethylene glycol.

A similar effect is shown in Table 1 when using Ru/Rh/NaOAc.3H$_2$O catalysts and 5 hour reaction times. A higher activity and selectivity is obtained in Example 5 (pressure 1500 bars) as compared with Example 12 (pressure 1300 bars).

EXAMPLES 49–51; COMPARATIVE EXAMPLE C5

These examples illustrate the use of tetraglyme as the liquid medium instead of acetic acid in the presence of Ru/Rh/2,2'-bipyridyl and 3-hydroxypyridine catalysts. The results are shown in Table 7. A typical experiment was conducted as follows. Tris-acetylacetonato-ruthenium (0.72 g, 1.8 mmoles), dicarbonylacetylacetonato-rhodium (0.05 g, 0.2 mmoles), 3-hydroxypyridine (0.48 g, 5.0 mmoles) and tetraglyme (50.5 g, 50 ml) were charged into a 100 ml glass liner. The liner was transferred into an Autoclave Engineers 150 ml magnedrive packless autoclave of A286 steel construction. The autoclave was sealed and after being

TABLE 5

| Ex No | Catalyst components mmoles Ru | Rh | 2,2'-bipyridyl | Total Pressure Bars | Pressure Drop Bars | MeOAc | EtOAc | EG Diacetate | EG Monoacetate | $\Sigma \begin{array}{c} CH_2OH \\ \| \\ CH_2OH \end{array}$ | EG/ MeOH |
|---|---|---|---|---|---|---|---|---|---|---|---|
| 40 | 2.0 | 0.2 | 1.0 | 1500 | 490 | 85.6 | 21.7 | 74.0 | 25.7 | 99.7 | 1.16 |
| 41 | 2.0 | 0.2 | 1.0 | 1250 | 260 | 64.1 | 14.6 | 42.9 | 10.7 | 53.6 | 0.84 |
| 42 | 2.0 | 0.2 | 1.0 | 1000 | 120 | 66.9 | 10.4 | 28.1 | 6.3 | 34.4 | 0.51 |
| 43 | 2.0 | 0.2 | 1.0 | 750 | 80 | 76.6 | 21.5 | 15.5 | 3.2 | 18.7 | 0.24 |

Notes on Table 5
1. Reaction conditions were under various pressures of CO/H$_2$ (1:1) at 235–240° C. for 2½ hours.
2. Ruthenium and rhodium were added as ruthenium tris-acetylacetonate [Ru(acac)$_3$] and rhodium acetate [Rh$_2$(OAc)$_4$.2MeOH] respectively.
3. Other products such as methyl formate and n-propyl acetate are also formed but are present in minor amounts, typically less than 2 mmole.

purged four times with a CO/H$_2$ mixture was pressurised to 500 bars with synthesis gas in a 1:1 ratio of CO:H$_2$. Stirring at a rate of 1100 rpm commenced. The autoclave was heated to 230° C. over a period of approximately 1 hour during which the pressure steadied at 750 bars. The pressure was then increased to 1550 bars and maintained at 1550-1450 bars by topping up with fresh gas over a 4 hour period. During this time a total pressure drop of 945 bars was recorded. After cooling overnight the excess pressure was slowly vented and the reaction product carefully discharged. The weight of reaction product (67.5 g) corresponded to a weight increase of ca. 15.7 g over the 4 hour reaction period. Analysis of the products by gas chromatography using a Porapak Q column showed ethylene glycol (99.7 mmoles) methanol (85.6 mmoles) and ethanol (37.4 mmoles) to be the major products.

Referring to Table 7, Examples 50 (Ru/Rh/2,2'-bipyridyl) and 51 (Ru/Rh/3-hydroxypyridine) illustrate good activity and good selectivity to ethylene glycol. In the absence of a co-catalyst, significantly increased yields of methanol are obtained by the addition of rhodium to ruthenium (Example 49 as compared with C5).

TABLE 7

| Ex No | Catalyst Components mmoles | | | Pressure drop bars | Product Analysis (mmoles) | | | |
|---|---|---|---|---|---|---|---|---|
| | Ru | Rh | Additive | | MeOH | MeOAc | EtOH | CH$_2$OH\|CH$_2$OH |
| 49 | 2.0 | 0.2 | 0 | 625 | 211.9 | 2.1 | 36.3 | 24.9 |
| 50 | 1.8 | 0.2 | 2.0 2,2'-bipyridyl | 810 | 101.3 | 10.3 | 36.4 | 108.1 |
| 51 | 1.8 | 0.2 | 5.0 3-hydroxypyridine | 945 | 85.6 | 10.3 | 37.4 | 99.7 |
| C5 | 2.0 | 0 | 0 | 500 | 103.3 | 6.3 | 29.9 | 29.7 |

Notes on Table 7
1. Reaction conditions were 1500 ± 50 bars of CO/H$_2$ (1:1) at 230° C. for 4 hours.
2. Ruthenium and rhodium were added as Ru(acac)$_3$ and Rh(CO)$_2$acac respectively.

EXAMPLES 52-55

The examples illustrate the effect of working at pressures of 750 bars to 210 bars. The results are shown in Table 8.

TABLE 8

| Ex No | Catalyst Components mmoles | | | Total Pressure Bars | Time Hour | Pressure drop bars | Products (mmoles) | | |
|---|---|---|---|---|---|---|---|---|---|
| | Ru | Rh | Additive | | | | MeOAc | Σ CH$_2$OH | EG/MeOH |
| 52 | 2.0 | 0.2 | 4.4 | 750 | 5.0 | 200 | 48.8 | 36.0 | 0.74 |
| 53 | 2.0 | 0.2 | 4.4 | 530 | 6.0 | 145 | 69.9 | 14.7 | 0.21 |
| 54 | 2.0 | 0.2 | 4.4 | 360 | 5.5 | 55 | 57.5 | 3.9 | 0.07 |
| 55 | 2.0 | 0.2 | 4.4 | 210 | 5.5 | 50 | 39.3 | 2.2 | 0.06 |

Notes on Table 8
Reaction conditions:
The additive was Cs$_2$CO$_3$.2H$_2$O
Temperature: 230° C.
CO/H$_2$ (1:1)
50 ml glacial acetic acid

I claim:

1. A process for the selective production of ethylene glycol and/or a carboxylic acid ester thereof which comprises contacting a mixture of carbon monoxide and hydrogen with a catalyst and a co-catalyst at a pressure of 500-3,000 bars in a liquid medium comprising a carboxylic acid, said catalyst comprising ruthenium and at least one other metal selected from rhodium, palladium, iridium, cobalt and nickel wherein the proportion of ruthenium is at least 50 percent by weight of rhe total weight of all of said metals and said co-catalyst comprising a compound of one or more metals of Group IA, IIA or IIB of the Periodic Table or nitrogen-containing cation and/or base, wherein the molar ratio of ruthenium to the total of said other metal is in the range 100:1 to 2:1.

2. The process of claim 1 wherein said other metal is rhodium,

3. The process of claim 1 wherein the ruthenium and/or said other metal are in elemental form, as a coordination compound or as a salt.

4. The process of claim 3 wherein the ruthenium and/or said other metal are present as a carbonyl, an acetyl acetonate or as a carboxylate.

5. The process of claim 4 wherein the carboxylate is an acetate or a benzoate.

6. The process of claim 1 wherein the compound of a Group IA, IIA or IIB metal is an oxide, hydroxide or salt.

7. The process of claim 6 wherein the salt is a carbonate, bicarbonate, nitrate, halide or carboxylate.

8. The process of claim 1 wherein the co-catalyst is a compound of one or more of the metals sodium, cesium and zinc.

9. The process of claim 1 wherein the nitrogen-containing cation and/or base is selected from ammonium salts, quaternary ammonium salts, iminium salts, pyridine, substituted pyridines, bipyridyls and phenanthrolines.

10. The process of claim 9 wherein the nitrogen-containing cation and/or base is selected from an ammonium carboxylate; a quaternary ammonium salt having the general formula (R$_4$N)$^+$X$^-$, wherein R, which may be the same or different, is alkyl, cyclohexyl, aryl, aralkyl or alkaryl, and X is hydroxide, nitrate, halide or carboxylate; an iminium salt having the general formula (R$_2$N)$^+$X$^-$ or [(R$_3$P)$_2$N]$^+$X$^-$ wherein R and X are as hereinbefore defined; alkyl, alkoxy and hydroxy pyridines, 2,2'-bipyridyl, 4,4'-bipyridyl and alkyl-substituted bipyridyls.

11. The process of claim 1 wherein the proportion by weight of liquid medium to catalyst is in the range 20:1 to 1,000:1.

12. The process of claim 1 wherein the molar concentration of co-catalyst to ruthenium and said other metal is in the range 0.05:1 to 100:1.

13. A process for the selective production of ethylene glycol and/or a carboxylic acid ester thereof which comprises contacting a mixture of carbon monoxide and hydrogen with a catalyst and a co-catalyst at a pressure of 500–2,000 bars in a liquid medium comprising a carboxylic acid, said catalyst comprising ruthenium and at least one other metal selected from rhodium, palladium, iridium, cobalt and nickel wherein the proportion of ruthenium is at least 50 percent by weight of the total weight of all of said metals and said co-catalyst comprising a compound of one or more metals of Group IA, IIA or IIB of the Periodic Table or a nitrogen-containing cation and/or base, wherein the molar ratio of ruthenium to the total of said other metal is in the range 100:1 to 2:1.

* * * * *